US005914417A

United States Patent [19]

Reichert et al.

[11] Patent Number: 5,914,417

[45] Date of Patent: Jun. 22, 1999

[54] NB, TA AND TI SALT SOLUTIONS AND PROCESSES FOR THE PRODUCTION AND USE THEREOF

[75] Inventors: Karlheinz Reichert, Wolfenbüttel; Wolfgang Simon; Harald Tröger, both of Goslar; Gisbert Ebeling, Hahnenklee, all of Germany

[73] Assignee: H.C. Starck GmbH & Co. KG, Goslar, Germany

[21] Appl. No.: 08/867,994

[22] Filed: Jun. 3, 1997

Related U.S. Application Data

[63] Continuation-in-part of application No. 08/582,168, Jan. 2, 1996, abandoned.

[30] Foreign Application Priority Data

Jan. 3, 1995 [DE] Germany ............................ 195 00 056

[51] Int. Cl.[6] .................................. C07F 9/00; C07F 7/00

[52] U.S. Cl. ................................ 556/42; 556/44; 556/54; 556/55

[58] Field of Search .................................. 556/42, 44, 54, 556/55

[56] References Cited

U.S. PATENT DOCUMENTS 3,523,128 8/1970 Bielecki et al. ........................ 260/429

FOREIGN PATENT DOCUMENTS 2 258 464 2/1993 United Kingdom .

OTHER PUBLICATIONS

Chemical Abstracts, vol. 95, Chemical Abstracts No. 122966, 1981.

*Primary Examiner*—Porfirio Nazario-Gonzalez
*Attorney, Agent, or Firm*—Jerry Cohen

[57] ABSTRACT

The present invention relates to novel organometallic compounds of the general formula $M(OH)_y(A)_V(B)_z$, wherein M is Ti(IV), Nb(V) or Ta(V) and x +y+z=5 for Nb and Ta and x+y+z=4 for Ti and A means an alkoxide ligand of diols and/or glycol monoethers and B is a carboxylate ligand of fatty acids of a carbon chain length of $C_6$–$C_{19}$, and to processes for the production and use thereof.

15 Claims, No Drawings

NB, TA AND TI SALT SOLUTIONS AND PROCESSES FOR THE PRODUCTION AND USE THEREOF

This application is a continuation-in-part of our patent application Ser. No. 08/582,168, filed Jan. 2, 1996 now abandoned.

BACKGROUND OF THE INVENTION

The present invention relates to novel organometallic compounds of the general formula $M(OH)_x(A)_y(B)_z$, wherein M means Ti(IV), Nb(V) and Ta(V) and x+y+z=5 for Nb and Ta and x+y+z=4 for Ti and A means an alkoxide ligand of diols and/or glycol monoethers and B means a carboxylate ligand of fatty acids of a carbon chain length of $C_6$–$C_{19}$, to a process for the production thereof and to the use thereof.

Various processes are known for the production of metal carboxylate solutions (Ullmann, volume 23, chapter 4.9, Metallseifen [metal soaps], page 224): one method for the production of such metal carboxylate solutions consists in reacting metal oxides, hydroxides or carbonates with corresponding fatty acids of a carbon chain length ot $C_6$–$C_{19}$ in mineral oils or hydrocarbons. Another production route comprises the so-called double reaction in which the sodium or potassium soaps of the corresponding fatty acids of a carbon chain length of $C_6$–$C_{19}$ are precipitated from a hot aqueous phase by adding salt solutions of the metals concerned, which are taken up in mineral oils or hydrocarbons in the second stage. This process is principally used for the metals cobalt, iron and manganese.

These processes cannot, however, successfully be used for metals such as Nb, Ta and Ti. No pure metal carboxylate compounds are known for these metals. According to Mater. Res. Soc. Symp. Proc. 60, 35 (1986), a titanium alkoxide/carboxylate compound of the formula $(Ti(OCH_3)_2(C_9H_{19}COO)_2$ is, however, known, which is usable for the above-stated purposes. However, this Ti compound does not exhibit long term stability. Comparable compounds of the type $M(OR)_x(OOCR)_y$ where M is Nb and Ta and x=3 and y=2 are not known. While these Ta or Nb compounds may indeed be prepared, they too do not exhibit the required properties, such as hydrolysis resistance and long term stability and miscibility with other metal carboxylate solutions. A further disadvantage of these alkoxide/carboxylate compounds is their residual sensitivity to hydrolysis and relatively high reactivity due to the remaining alkoxide groups, which gives rise to problems during further processing and the production of mixtures.

The object of the present invention is thus to provide organometallic compounds based on Nb, Ta and Ti which do not exhibit the disadvantages of the prior art.

SUMMARY OF THE INVENTION

It has now been found that these requirements are satisfied by organometallic compounds of the general formula $M(OH)_x(A)_y(B)_z$, wherein M is Ti(IV), Nb(V) and Ta(V) and x+y+z=5 for Nb and Ta and x+y+z=4 for Ti and A is an alkoxide ligand of diols andlor glycol monoethers and B is a carboxylate ligand of fatty acids of a carbon chain length of $C_6$–$C_{19}$. 2-Methyl-2,4- pentanediolate is preferred as A and 2-ethylhexanoate as B. In a particularly preferred embodiment, these substances are dissolved in hydrocarbons.

Preferrably each of x, y and z is present in a finite amount that is functionally significant and preferrably at x of at least 1.0 with y of at least 0.1 (more preferrably 0.3) and/or y of at least 0.1 (more preferrably 0.3).

This invention also provides a process for the production of the organometallic compounds according to the invention which is characterized in that metal alkoxides of the general formula $M(OR)_5$ for Ta or Nb or $M(OR)_4$ for Ti, wherein R are organic residues, dissolved in hydrocarbons, are reacted in succession (sequence) with carboxylic acids, diols and/or glycol monoethers and water to yield the above-stated compounds and the liberated alcohol ROH is simultaneously removed.

DETAILED DESCRIPTION OF PREFERRED EMBODIMENTS

Particularly good results are achieved if replacing single or sets of alkoxide groups by carboxylic acids and then a further single or sets of alkoxide groups are replaced diols or glycol monoethers and then a final alkoxide hydrolyzed with water. For example, and preferrably, two of the alkoxide groups on the Ta or Nb alkoxide are first replaced by two carboxylic acids of a carbon chain length of $C_6$–$C_{19}$, while simultaneously removing the liberated alcohol and then two further alkoxide groups are replaced by diols or glycol monoethers while simultaneously removing the liberated alcohol. The remaining, final alkoxide group on the resultant Ta/Nb compound is hydrolyzed with water.

It has also proved advantageous if two of the alkoxide groups of the titanium alkoxide are first replaced by two carboxylic acids of a carbon chain length of $C_6$–$C_{19}$, while simultaneously removing the alcohol and then only one further alkoxide group is replaced by a diol or glycol monoether while simultaneously removing the alcohol. In this case too, as with Ta and Nb, the final alkoxide group is hydrolyzed by the addition of water.

It has surprisingly been found that solutions produced in this manner are resistant to hydrolysis. Water may thus be added to the Ta or Nb solution according to the invention without hydrolysis occurring after 24 hours. The Ti carboxylate solution according to the invention is so stable that it is even possible to heat it to 100° C. in the presence of water. On the basis of these extreme conditions, it may be assumed that this compound also has extended long term stability.

The metal salt solutions obtained according to the invention may advantageously be further processed in the following ways:

1. A stable gel is obtained by removing the solvent. This gel may be converted into the corresponding finely divided metal oxide by calcination.

2. Another embodiment of such further processing is the precipitating of metal oxide-hydrates, preferably by adding amrnonia, which oxide-hydrates, once filtered, dried and calcined, give rise to the corresponding finely divided oxide.

3. Stable, multi-component solutions, which are for example of interest for electro-cerarnics, may be produced from the metal salt solutions obtained according to the invention. Thus, for example, the titanium salt solution obtained according to the invention may straightforwardly be mixed with a barium carboxylate solution. This mixture may be further processed in the same manner as the pure carboxylate solutions (see points 1 and 2 above). Other basic components containing titanium for electro-ceramics, such as for example lead titanate, lead zirconium titanate, strontium titanate etc. may also be obtained via similar metal carboxylate mixtures. Basic components containing niobium and/or Ta for electro-ceramics may also be produced in the same manner, such as, for example, lead magnesium niobate, lead nickel niobate, barium magnesium tantalate and barium zinc tantalate.

After further processing as described under points 1 and 2 above, very homogeneous and reactive intermediates, which may be reacted even at very low temperatures, are obtained from this multi-component solution. Thus, for example, the pyrochlore phase is obtained from the precipitated PMN intermediate at temperatures as low as 300° C. At 500° C., this pyrochlore changes into the desired perovskite. Perovskite content is above 80% after a calcination time of 3 hours (h) at 700° C. Calcination temperatures are initially dependent upon the resultant perovskite However, due to the elevated reactivity of the intermediates obtained using the process according to the invention, these temperatures are distinctly lower than in the ceramic process. Calcination is particularly advantageously performed over a range from 30 minutes to 4 hours.

4. By adding film-forming auxiliary substances to the metal salt solutions and multi-component solutions obtained according to the invention, it is possible to produce stable solutions which may be further processed into films with metal contents of >10%. The present invention also provides this use.

5. The stable solutions produced in point 4 may also be combined with the corresponding metal oxides to yield stable dispersions which may also be further processed into films with metal contents of >50%. The films stated in points 4 and 5, above, may be of interest for the production of thin dielectric layers of <10$\mu$. The present invention provides this use too.

The invention is illustrated below by way of non-limiting examples.

EXAMPLES

Comparative example I

Production of metal carboxylate solutions, as are, for example, used in the paint and lacquer industry.

1 mol of PbO or ZnO or MgO or $E_2O_3$ (E=rare earth metal) or $Zr_2(CO_3)(0H)_2O_2$ or $Ba(OH)_2$ or $Sr(OH)_2$ or $Co(OH)_2$ was added in portions to a mixture of 2-ethylhexanoic acid in mineral spirits and slowly heated to 100° C. The resultant water of reaction was removed from the mixture under reduced pressure. A clear solution was obtained. The selected quantity of 2-ethylhexanoic acid was substoichiometric, hyperstoichiometric or stoichiometric as required.

Example 1

Production of an Nb metal carboxylate solution

One mol of $Nb(OEt)_5$ was diluted with 200 g of mineral spirits and stirred. The mixture was heated to 60° C. and 2 mol of 2-ethylhexanoic acid were added 2 mol of ethanol were liberated, which were removed by distillation at 60° C. under reduced pressure. I mol of diol (for example: 2-methyl-2,4- pentanediol) were added in a second stage. The ethanol so liberated was also removed by distillation. One mol of water was then slowly run in. The liberated ethanol (1 mol) was removed by distillation. The resultant mixture is adjusted to a metal content of 10% with mineral spirits.

Example 2

Production of a Ti metal carboxylate solution

One mol of isopropyl titanate was diluted with an equal quantity of mineral spirits and was slowly combined with 2 mol of 2-ethylhexanoic acid while being stirred. 2 mol of isopropanol were liberated which were removed by distillation at 60° C. under reduced pressure. 0.5 mol of diol (for example: 2-methyl-2,4-pentanediol) were added in a second stage. Isopropanol was again liberated, which was removed from the solution under reduced pressure. In the final stage, 1 mol of water was slowly added dropwise and the alcohol so liberated was removed by distillation. The resultant mixture was finally adjusted to the desired metal content.

Example 3

Production of a multi-component solution consisting of lead, magnesium and niobium carboxylate To this end, 155 g of a niobium carboxylate solution (see example 1) with an Nb content of 12% Nb, 260 g of a lead carboxylate solution with a metal content of 24% Pb and 60 g of a magnesium carboxylate solution with an Mg content of 4% Mg were mixed together. The resultant hydrolysis-resistant. Storage stable mixed metal solution has a Pb:Mg:Nb molar ratio of 3:1:2.

Example 4

Production of a multi-component solution consisting of lead, zirconium and titanium carboxylate.

To this end, 115 g of a lead carboxylate solution with a Pb content of 36% Pb, 51 g of a zirconium carboxylate solution with a Zr content of 18% Zr and 60 g of a titanium carboxylate solution (see example 2) with a Ti content of 8% Ti were mixed together. The resultant hydrolysis-resistant, storage-stable mixed metal solution has a Pb :Zr:Ti molar ratio of 2:1:1.

Example 5

Production of a multi-component solution consisting of barium and titanium carboxylate To this end, 110 g of a barium carboxylate solution with a Ba content of 12.5% Ba and 60 g of a titanium carboxylate solution (see example 2) with a Ti content of 8% Ti were mixed together. The resultant hydrolysis-resistant, storage-stable mixed metal solution has a Ba:Ti molar ratio of 1:1.

Example 6

Production of a typical grinding composition, which may be further processed into green film.

50 g of water are first introduced into a stirred vessel. 60 g of lead magnesium niobate powder (pure perovskite phase), 0.5 g of Borchigen DFN (Borchers GmbH, Monheim), 0.5 g of ammonia (25%) and 1 g of Borchigel L75N (Borchers GmbH, Monheim) were then added in succession while being gently stirred. After adding 110 g of glass beads (diameter 2 mm), the mixture was dispersed for approximately 45 minutes using a bead mill (1800 rpm). The dispersion was then formulated, with slow stirring, into a lacquer with Acronal 290 D polymer dispersion (commercial product of BASF AG). After screening out the glass beads, 45 g of the mixture stated in example 3 and 5 g of Atlox 1045 A (commercial product of ICI) were then added to 200 g of the lacquer. This resultant lacquer mixture was homogenized by slow stirring and could then be applied after a maturation period of 3 hours.

Information Concerning the Auxiliary Substances Used

Borchigen DFN: aromatic polyglycol ether

Borchigel L75N: non-ionic thickener based on a hydrophobized polyether urethane copolymer (50% in water)

Acronal 290 D: dispersion of a butyl acrylate and styrene copolymer (50% in water)

Atlox 1045 A: polyoxyethylene sorbitol oleate laurate

Example 7

Production of lead magnesium niobate 100 g of a PMN carboxylate solution obtained from example 3 were concentrated until a clear, transparent gel was obtained. This gel was calcined for 2 hours at 800° C. The powder obtained in this manner is a virtually pure-phase perovskite with a pyrochlore content of <2%.

Example 8

Production of lead magnesium niobate 100 g of a PMN carboxylate solution obtained from example 3 were combined with approximately 40 ml of a 25% $NH_4OH$ solution. A quantitative amount of a fme, white precipitate is produced, which was separated by filtration. The filtration residue was dried at 105° C. and then calcined at 800° C. for 2 hours. The powder obtained in this manner is also a virtually pure-phase perovskite with a pyrochlore content of <2%.

Example 9

Production of niobium oxide 100 g of an Nb carboxylate solution (example 1) with a niobium content of 10% were concentrated to a clear, transparent gel. This gel was decomposed at 800° C. The powder obtained in this manner is a pure-phase niobium oxide (T phase).

Example 10

Production of barium titanate.

100 g of a Ba-Ti carboxylate solution obtained from example 5 were concentrated until a clear, transparent gel is obtained. This gel was calcined for 4 hours at 900° C. According to X-ray diffraction analysis, the resultant powder is a purephase perovskite.

Example 11

Production of barium titanate.

100 g of a Ba-Ti carboxylate solution obained from example 5 were combined with approximately 40 ml of a 25% $NH_4OH$ solution. A fine, white precipitate is produced, which was filtered out and washed with methanol. This precipitate was dried at 105° C. and then calcined at 800° C. for 4 h. The powder obtained in this manner is also a pure-phase perovskite.

Example 12

Test for hydrolysis resistance (comparison with pure alkoxide carboxylate solutions or alkoxide solutions).

50 g of a solution of the Nb or Ta compound according to the invention in mineral spirits (metal content 10% in each case) were stirred with 5 g of water at room temperature. Even after 24 hours' stirring, this mixture exhibited neither turbidity nor precipitation, whereas comparable solutions of $Nb(OEt)_5$, $Nb(OR)_4(OOH_3)_2Ta(OEt)_5$ and $Ta(OR)_3(OOCR)_2$ immediately became turbid and formed a precipitate on addition of water.

Example 13

Test for hydrolysis resistance.

50 g of a solution of the Ti compound according to the invention in mineral spirits and 50 g of a solution of $Ti(OCH_3)_2(C_9H_{19}COO)_2$ in mineral spirits (metal content 5% in each case) were combined with 5 g of water and stirred while being heated. In the case of the Ti compounds according to the invention, water could be distilled off from this mixture at a temperature of >100° C. without resulting in turbidity or precipitation in the organic solution, whereas the mixture of the solution of $Ti(OCH_3)_2(CgH_{,9}COO)_2$ in mineral spirits with water released methanol at a temperature of >70° C. and became turbid over the course of the treatment.

Example 14

Production of a Nb metal carboxylate solution.

0.5 mol of $Nb(OEt)_5$ was diluted with 200 g of mineral spirits and stirred. The mixture was heated to 60° C. and1 mol of neodecanoic acid was added. 1 mol of ethanol evolved, which was distilled off at 60° C. under reduced pressure. In a second step 1 mol of glycol monoether (butylene glycol) was added. The ethanol liberated was distilled off. Then 0.5 mol of water was added to the mixture The ethanol once again liberated was distilled off. The resulting solution was adjusted to a metal content of 8% using mineral spirits.

Example 15

Production of a Nb metal carboxylate solution 1 mol of $Nb(OEt)_5$ was diluted with 200 g of mineral spirits and stirred. The mixture was heated to 60° C. and 2 mols of neodecanoic acid were added. 2 mols of ethanol evolved, which were distilled off at 60° C. under reduced pressure. In a second step 1 mol of diol (2-methylpentane-2,4-diol) was added. The ethanol liberated was distilled off. Then 1 mol of water was added to the mixture. The ethanol once again liberated was distilled off. The resulting solution was adjusted to a metal content of 10% using mineral spirits.

Example 16

Production of a Ta metal carboxylate solution 1 mol of $Ta(OEt)_5$ was diluted with 200 g of mineral spirits and stirred. The mixture was heated to 60° C. and 2 mols of 2-ethylhexanoic acid were added. 2 mols of ethanol evolved, which were distilled off at 60° C. under reduced pressure. In a second step 1 mol of diol (2-methylpentane-2,4-diol) was added. The ethanol liberated was distilled off. Finally 1 mol of water was added to the mixture. The ethanol once again liberated was distilled off. The resulting solution was adjusted to a metal content of 10% using mineral spirits.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Organometallic compounds of the general formula $M(OH)_x(A)_y(B)_z$, characterized in that M is a metal selected from the group consisting of Ti(IV), Nb(V) and Ta(V), x+y+z=5 for Nb and Ta and x+y+z=4 for Ti, and A is an alkoxide ligand of diols and/or glycol monoethers and B is a carboxylate ligand of fatty acids of a carbon chain length of $C_6$–$C_{19}$ and wherein each of x, y and z is larger than zero.

2. Organometallic compounds according to claim 1, wherein x is at least 1, and y is at least 0.1 and z is at least 0.1.

3. Organometallic compounds according to claim 2, wherein x is at least 1, and y is at least 0.3 and z is at least 0.3.

4. Process for the production of organometallic compounds as defined in any of claims 1, 2 or 3 of the general formula $M(OH)_x(A)_y(B)_z$, characterized in that M is a metal selected from the group consisting of Ti(IV), Nb(V) and Ta(V), x+y+z=5 for Nb and Ta and x+y+z=4 for Ti, and A is an alkoxide ligand of diols and/or glycol monoethers and B is a carboxylate ligand of fatty acids of a carbon chain length of $C_6$–$C_{19}$, characterized in that metal alkoxide of the general formula $M(OR)_5$ for Ta or Nb or $M(OR)_4$ for Ti, wherein R is organic residues, dissolved in hydrocarbons, are reacted with two or more reagents selected from the class consisting of carboxylic acids, diols and glycol monoethers and further hydrolized with water to yield the above-stated compounds and wherein the liberated alcohol ROH is simultaneously removed.

5. Process according to claim 4 wherein M is Ta or Nb and two of the alkoxide groups of the Ta or Nb alkoxide are first replaced by a carboxylic acid of a carbon chain length of $C_6$–$C_{19}$ while simultaneously removing the alcohol and then two further alkoxide groups are replaced by a diol or glycol monoether while simultaneously removing the alcohol and the final alkoxide group is hydrolyzed by water.

6. Process according to claim 4 wherein M is Ti and two of the alkoxide groups of the titanium alkoxide are first replaced by a carboxylic acid of a carbon chain length of $C_6$–$C_{19}$ while simultaneously removing the alcohol and then one further alkoxide group is replaced by a diol or glycol monoether while simultaneously removing the alcohol and the final alkoxide group is hydrolyzed by water.

7. Organometallic compounds according to any of claims 1, 2 or 3, characterized in that A is 2-methyl-2,4-pentanediolate and B is 2-ethylhexanoate.

8. Organometallic compounds according to either of claims 1 or 2, characterized in that they are in dissolved form in hydrocarbons.

9. Process for the production of organometallic compounds of the general formula $M(OH)_x(A)_y(B)_z$, characterized in that M is a metal selected from the group consisting of Nb(V) and Ta(V), x+y+z=5 where each of x, y and z is greater than zero, and A is an alkoxide ligand selected from the class consisting of of diols and/or glycol monoethers and B is a carboxylate ligand of fatty acids of a carbon chain length of $C_6$–$C_{19}$, characterized in that metal alkoxide of the general formula $M(OR)_5$ wherein R comprises one or more organic residues, dissolved in hydrocarbons, is reacted with two or more reagents selected from the class consisting of carboxylic acids, diols and glycol monoethers and further hydrolyzed with water to yield the above-stated compounds and wherein the liberated alcohol ROH is simultaneously removed.

10. Process in accordance with claim 9 wherein two of the alkoxide groups of Ta or Nb alkoxide are first replaced by two carboxylic acids of a carbon chain length of $C_6$–$C_{19}$, while simultaneously removing the liberated alcohol ROH and then two further alkoxide groups are replaced by diols or glycol monoethers while simultaneously removing the liberated alcohol ROH and the final alkoxide group is hydrolyzed with water.

11. Process for the production of organometallic compounds of the general formula $Ti(OH)_x(A)_y(1B)_z$, and x+y+z=4, and A is an alkoxide ligand of diols and/or glycol monoethers and B is a carboxylate ligand of fatty acids of a carbon chain length of $C_6$–$C_{19}$, and further characterized in that a metal alkoxide of the general formula $Ti(OR)_4$, wherein R is one or more organic residue, dissolved in hydrocarbon, is reacted with one or more reagents selected from the class consisting of carboxylic acids, diols and glycol monoethers and water to yield the above-stated compounds and wherein the liberated alcohol ROH is simultaneously removed, and further characterized in that, two of the alkoxide groups of the titanium alkoxide are first replaced by a carboxylic acid of a carbon chain length of $C_6$–$C_{19}$ while simultaneously removing the alcohol ROH and then one further alkoxide group removing the alcohol or glycol monoether while simultaneously removing the alcohol and the final alkoxide group is hydrolyzed by water.

12. Process according to either of claims 10 or 11 wherein the organometallic compounds thereof or multi-component systems containing these compounds are further treated with the addition of film-forming auxiliary substances for the production of films with a metal content of >10%.

13. Process according to either of claims 10 or 11 wherein the organometallic compounds thereof or multi-component systems containing these compounds are further treated with the addition of milm-forming auxiliary substances for the production of films from stable dispersions with the addition of metal oxides of the same species with a metal content of >50%.

14. Process of treatment of the organometallic compounds or multi-component systems of any of claims 1, 2 or 3, containing these compounds by treating the same by adding thereto film-forming auxiliary substances for the production of films with a metal content of >10%.

15. Process of treatment of the organometallic compounds thereof or multi-component systems of any of claims 1, 2 or 3, containing these compounds by adding thereto film-forming auxiliary substances for the production of films from stable dispersions with the addition of metal oxides of the same species with a metal content of >50%.

* * * * *